(12) United States Patent
Takenaka

(10) Patent No.: US 8,878,134 B2
(45) Date of Patent: Nov. 4, 2014

(54) PHOTOCONDUCTIVE ANTENNA, TERAHERTZ WAVE GENERATING DEVICE, CAMERA, IMAGING DEVICE, AND MEASURING DEVICE

(71) Applicant: Seiko Epson Corporation, Tokyo (JP)

(72) Inventor: Satoshi Takenaka, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 138 days.

(21) Appl. No.: 13/721,960

(22) Filed: Dec. 20, 2012

(65) Prior Publication Data

US 2013/0181128 A1    Jul. 18, 2013

(30) Foreign Application Priority Data

Jan. 18, 2012   (JP) ................... 2012-007939

(51) Int. Cl.
   *G01J 5/02*     (2006.01)
   *H01L 31/16*    (2006.01)
   *H01L 33/00*    (2010.01)

(52) U.S. Cl.
   CPC ............ *H01L 33/0004* (2013.01); *H01L 31/16* (2013.01)
   USPC ..................................... 250/341.1

(58) Field of Classification Search
   CPC ................. G01N 21/3586; G02F 2203/13
   USPC ............................... 250/330, 341.1
   See application file for complete search history.

(56) References Cited

U.S. PATENT DOCUMENTS

| | | | |
|---|---|---|---|
| 6,320,191 B1 * | 11/2001 | Rudd | 250/341.1 |
| 6,738,397 B2 | 5/2004 | Yamamoto et al. | |
| 8,067,754 B2 * | 11/2011 | Kasai | 250/493.1 |
| 8,093,560 B2 | 1/2012 | Kuroyanagi et al. | |
| 8,481,939 B2 * | 7/2013 | Kajiki | 250/336.1 |
| 2008/0315098 A1 * | 12/2008 | Itsuji | 250/330 |
| 2010/0052083 A1 * | 3/2010 | Kasai | 257/431 |
| 2011/0057206 A1 * | 3/2011 | Sartorius et al. | 257/85 |

FOREIGN PATENT DOCUMENTS

| | | | |
|---|---|---|---|
| JP | 2002-223017 A | 8/2002 |
| JP | 2003-015175 A | 1/2003 |
| JP | 2006-010319 A | 1/2006 |
| JP | 2006-145372 A | 6/2006 |

(Continued)

OTHER PUBLICATIONS

Kiyomi Sakai et al.; Terahertz Electromagnetic Waves; Generation and Applications; "Laser Studies" Academic Journal of the Laser Society of Japan, vol. 26, No. 7; Jul. 1998.

(Continued)

*Primary Examiner* — Kiho Kim
(74) *Attorney, Agent, or Firm* — Global IP Counselors, LLP

(57) ABSTRACT

A photoconductive antenna is adapted to generate terahertz waves when irradiated by pulsed light. The photoconductive antenna includes a first conductive region, a second conductive region, and a semiconductor region. The second conductive region is spaced apart from the first conductive region to form a gap therebetween in a top plan view of the photoconductive antenna. The semiconductor region is positioned in the gap between the first conductive region and the second conductive region in the top plan view. An interfacial surface of the semiconductor region positioned in the gap is flush with first interfacial surfaces of the first and second conductive regions. Second interfacial surfaces of the first and second conductive regions positioned on an opposite side from the first interfacial surfaces are positioned on the same side with respect to the interfacial surface of the semiconductor region positioned in the gap.

24 Claims, 13 Drawing Sheets

(56) References Cited

FOREIGN PATENT DOCUMENTS

| | | |
|---|---|---|
| JP | 2006-313803 A | 11/2006 |
| JP | 2009-124437 A | 6/2009 |
| JP | 2010-050287 A | 3/2010 |

OTHER PUBLICATIONS

S.M. Sze; Semiconductor Device (vol. 15); p. 36, Fig. 7 and p. 104, Fig. 27; Jun. 14, 2002.

* cited by examiner

PHOTOCONDUCTIVE ANTENNA, TERAHERTZ WAVE GENERATING DEVICE, CAMERA, IMAGING DEVICE, AND MEASURING DEVICE

CROSS-REFERENCE TO RELATED APPLICATIONS

This application claims priority to Japanese Patent Application No. 2012-007939 filed on Jan. 18, 2012. The entire disclosure of Japanese Patent Application No. 2012-007939 is hereby incorporated herein by reference.

BACKGROUND

1. Technical Field

The present invention relates to a photoconductive antenna, a terahertz wave generating device, a camera, an imaging device, and a measuring device.

2. Related Art

In recent years, attention has been devoted to terahertz waves, which are electromagnetic waves with frequencies of 100 GHz or greater and 30 THz or less. Terahertz waves can be used in various forms of measurement and non-destructive testing such as imaging and spectrometry.

The terahertz wave generating device that generates these terahertz waves has a light source device that generates light pulses (pulsed light) having pulse widths at the approximately sub picosecond level (several hundred femtoseconds) and a photoconductive antenna that generates terahertz waves by irradiating light pulses generated by the light pulse generator.

As the photoconductive antenna, for example, disclosed in Japanese Laid-Open Patent Application Publication No. 2010-50287 is a pin structure photoconductive element (photoconductive antenna) which has an n type semiconductor layer, an i type semiconductor layer, and a p type semiconductor layer. With this photoconductive antenna, the n type semiconductor layer is provided at one surface side of the i type semiconductor layer, and the p type semiconductor layer is provided at the other surface side. Also, the n type semiconductor layer and the p type semiconductor layer are arranged to be skewed in relation to each other in the thickness direction of the i type semiconductor layer. Note that the terahertz waves are emitted in the direction perpendicular to the direction of the electric field.

With the photoconductive antenna noted in the above mentioned publication, for a dipole shaped photoconductive antenna (PCA) manufactured using a low temperature growth GaAs (LT-GaAs) substrate, it is possible to make the intensity of the generated terahertz waves approximately 10 times larger.

SUMMARY

With the photoconductive antenna noted in the above mentioned publication, the n type semiconductor layer is provided on one surface side of the i type semiconductor layer, and the p type semiconductor layer is provided on the other surface side, so the electric field direction changes according to variation in the thickness of the i type semiconductor during manufacturing, and because of that, there is the problem that variation occurs in the terahertz wave emission direction.

An object of the present invention is to provide a photoconductive antenna, a terahertz wave generating device, a camera, an imaging device, and a measuring device capable of suppressing variation in the emission direction, and generating high intensity terahertz waves.

This kind of object is achieved by the aspects of the present invention noted hereafter.

A photoconductive antenna according to one aspect of the present invention is adapted to generate terahertz waves when irradiated by pulsed light. The photoconductive antenna includes a first conductive region, a second conductive region, and a semiconductor region. The first conductive region is made of a semiconductor material containing a first conductive type impurity. The second conductive region is made of a semiconductor material containing a second conductive type impurity different from the first conductive type impurity. The second conductive region is spaced apart from the first conductive region to form a gap therebetween in a top plan view of the photoconductive antenna. The semiconductor region is positioned in the gap between the first conductive region and the second conductive region in the top plan view, and made of a semiconductor material having a carrier density that is lower than a carrier density of the semiconductor material of the first conductive layer or a carrier density of the semiconductor material of the second conductive layer. An interfacial surface of the semiconductor region positioned in the gap is flush with a first interfacial surface of the first conductive region and a first interfacial surface of the second conductive region. A second interfacial surface of the first conductive region positioned on an opposite side from the first interfacial surface and a second interfacial surface of the second conductive region positioned on an opposite side from the first interfacial surface are positioned on the same side with respect to the interfacial surface of the semiconductor region positioned in the gap.

With this configuration, it is possible to make the electric field direction constant, and thus, it is possible to suppress variation in the terahertz wave emission direction, making it possible to generate high intensity terahertz waves.

With the photoconductive antenna according to the above described aspect of the present invention, the gap between the first conductive region and the second conductive region is preferably filled by the semiconductor region.

With this configuration, it is possible to generate higher intensity terahertz waves.

The photoconductive antenna according to the above described aspect of the present invention preferably further includes a first electrode disposed on the first conductive region and electrically connected to the first conductive region with the first electrode having the same shape as the first conductive region in the top plan view.

With this configuration, it is possible to lower the contact resistance of the first conductive region and the first electrode, making it possible to reduce the power consumption.

The photoconductive antenna according to the above described aspect of the present invention preferably further includes a second electrode disposed on the second conductive region and electrically connected to the second conductive region, the second electrode having the same shape as the second conductive region in the top plan view.

With this configuration, it is possible to lower the contact resistance between the second conductive region and the second electrode, making it possible to reduce the power consumption.

The photoconductive antenna according to the above described aspect of the present invention preferably further includes an insulation region disposed over at least a portion of the interfacial surface of the semiconductor region positioned in the gap between the first conductive region and the second conductive region in the top plan view.

With this configuration, it is possible to more reliably prevent the occurrence of leaked current at the gap between the first conductive region and the second conductive region.

With the photoconductive antenna according to the above described aspect of the present invention, the semiconductor material of the semiconductor region is preferably a III-V compound.

With this configuration, it is possible to generate higher intensity terahertz waves.

A terahertz wave generating device according to another aspect of the present invention includes the photoconductive antenna according to the above mentioned aspects, and a light source configured and arranged to generate the pulsed light.

With this configuration, it is possible to provide a terahertz wave generating device having the effects of the present invention.

A camera according to another aspect of the present invention includes the photoconductive antenna according to the above mentioned aspects, a light source configured and arranged to generate the pulsed light, and a terahertz wave detecting unit configured and arranged to detect the terahertz waves emitted from the photoconductive antenna and reflected by an object.

With this configuration, it is possible to provide a camera having the effects of the present invention.

An imaging device according to another aspect of the present invention includes the photoconductive antenna according to the above mentioned aspects, a light source configured and arranged to generate the pulsed light, a terahertz wave detecting unit configured and arranged to detect the terahertz waves emitted from the photoconductive antenna and transmitted through an object or reflected by the object, and an image forming unit configured and arranged to generate an image of the object based on detection results of the terahertz wave detecting unit.

With this configuration, it is possible to provide an imaging device having the effects of the present invention.

A measuring device according to another aspect of the present invention includes the photoconductive antenna according to the above mentioned aspects, a light source configured and arranged to generate the pulsed light, a terahertz wave detecting unit configured and arranged to detect the terahertz waves emitted from the photoconductive antenna and transmitted through an object or reflected by the object, and a measuring unit configured and arranged to measure the object based on detection results of the terahertz wave detecting unit.

With this configuration, it is possible to provide a measuring device having the effects of the present invention.

BRIEF DESCRIPTION OF THE DRAWINGS

Referring now to the attached drawings which form a part of this original disclosure.

DETAILED DESCRIPTION OF EXEMPLARY EMBODIMENTS

Following, a detailed description of the photoconductive antenna, the terahertz wave generating device, the camera, the imaging device, and the measuring device of the present invention will be provided based on preferred embodiments shown in the attached drawings.

First Embodiment

Figure 1:
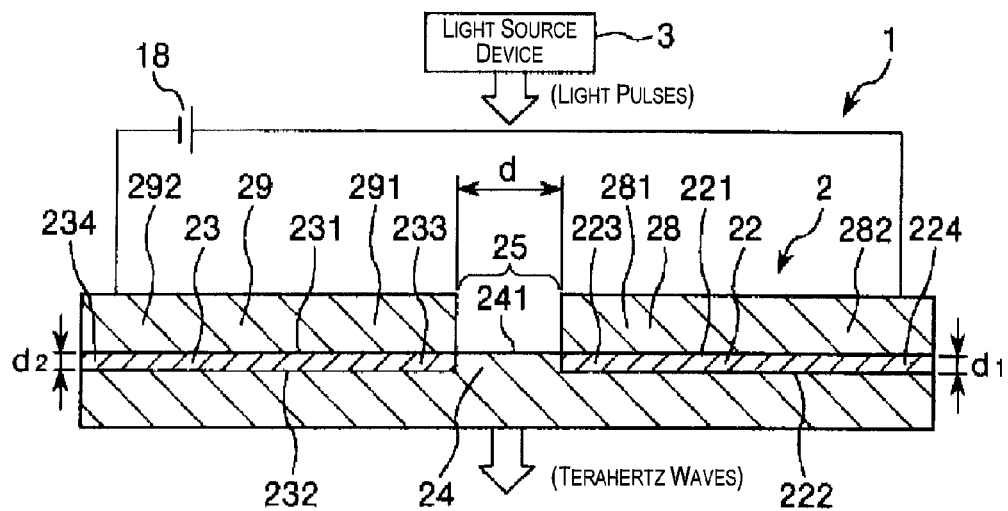
FIG. 1 is a drawing showing a terahertz wave generating device (photoconductive antenna) according to a first embodiment of the present invention as taken along a section line S-S in FIG. 2.
Figure 2:
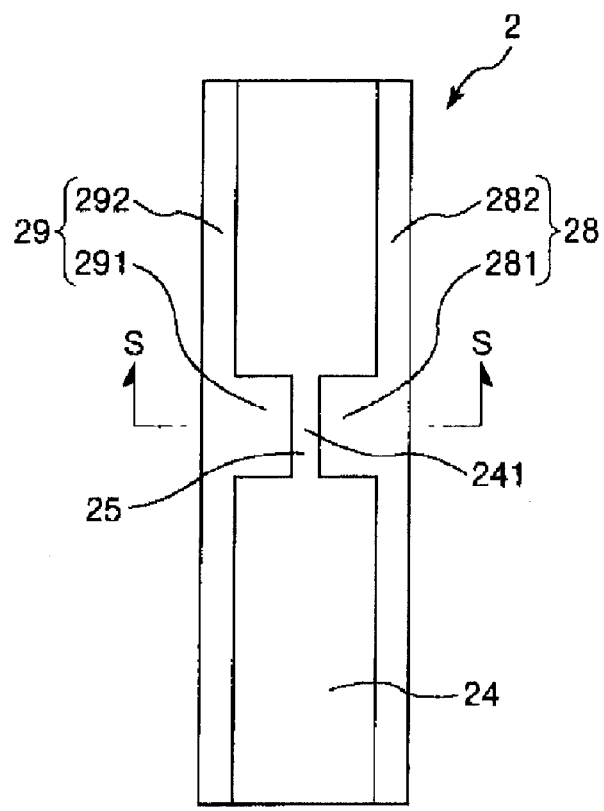
FIG. 2 is a top plan view of the photoconductive antenna of the terahertz wave generating device shown in FIG. 1.
Figure 3A:
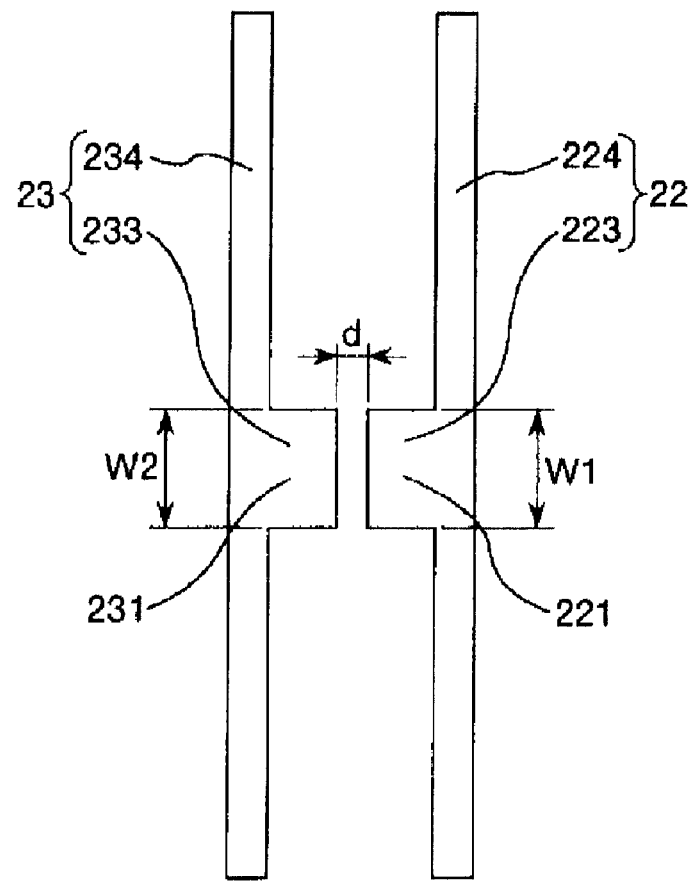
FIG. 3A is a top plan view of the n type semiconductor layer and the p type semiconductor layer of the photoconductive antenna of the terahertz wave generating device shown in FIG. 1.
Figure 3B:
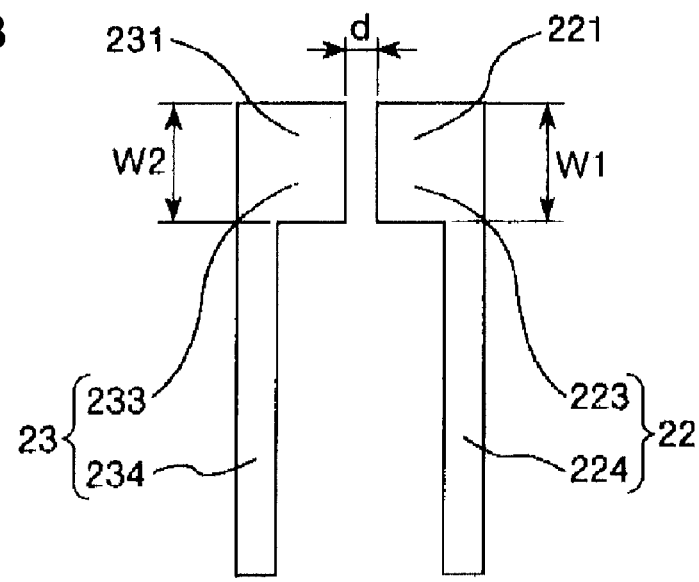
FIG. 3B is a top plan view of the n type semiconductor layer and the p type semiconductor layer of the photoconductive antenna in an alternative embodiment.
Figure 4:
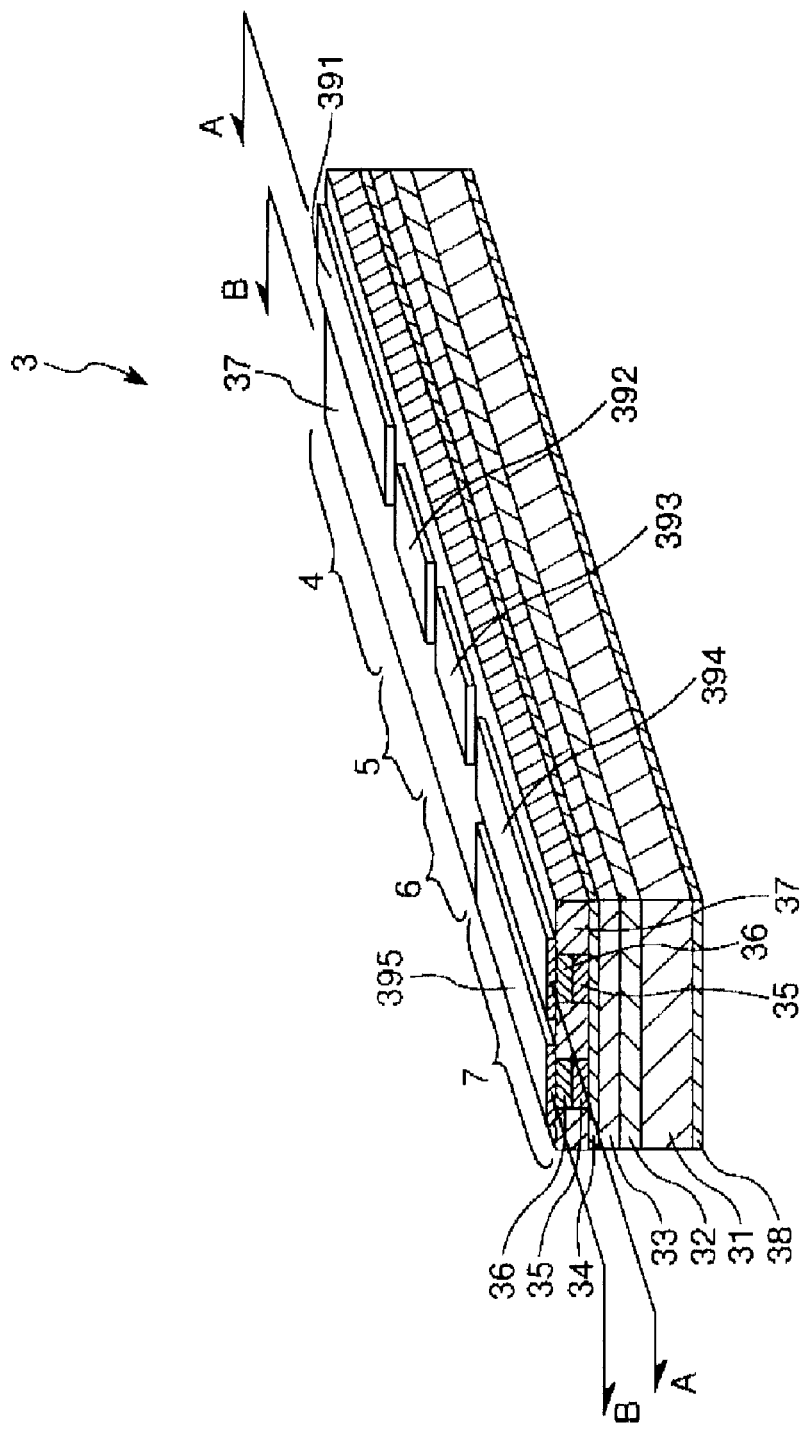
FIG. 4 is a cross section perspective view of the light source device of the terahertz wave generating device shown in FIG. 1.
Figure 5:
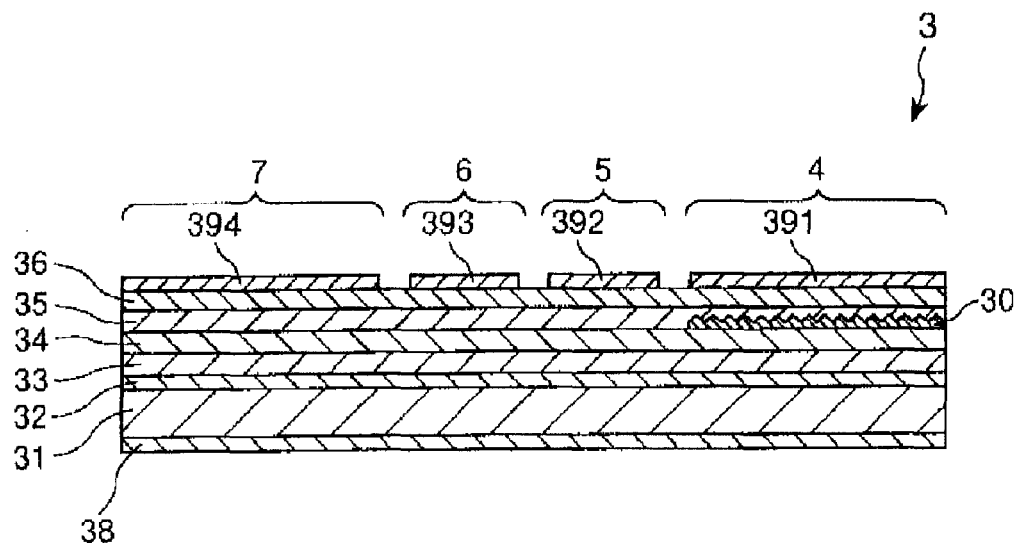
FIG. 5 is a cross section view of the light source device as taken along a section line A-A in FIG. 4.
Figure 6:
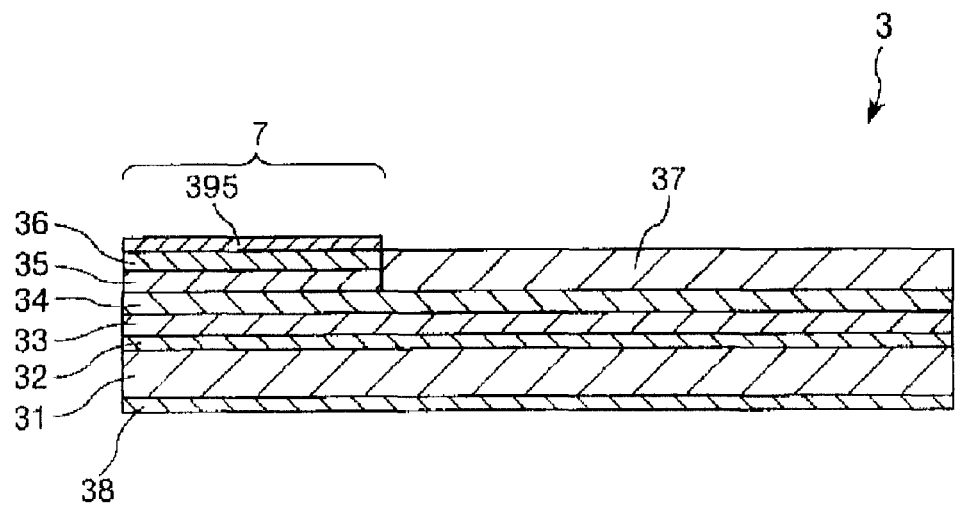
FIG. 6 is a cross section view of the light source device as taken along a section line B-B in FIG. 4.

FIG. 1 is a drawing showing the terahertz wave generating device according to the first embodiment of the present invention. With this FIG. 1, a cross section view taken along a section line S-S in FIG. 2 is shown for the photoconductive antenna, and a block diagram is shown for the light source device. FIG. 2 is a top plan view of the photoconductive antenna of the terahertz wave generating device shown in FIG. 1. FIG. 3A is a top plan view of the n type semiconductor layer and the p type semiconductor layer of the photoconductive antenna of the terahertz wave generating device shown in FIG. 1, while FIG. 3B shows a top plan view of the n type semiconductor layer and the p type semiconductor layer of the photoconductive antenna of the terahertz wave generating device in an alternative embodiment. FIG. 4 is a cross section perspective view of the light source device of the terahertz wave generating device shown in FIG. 1. FIG. 5 is a cross section view taken along a section line A-A in FIG. 4. FIG. 6 is a cross section view taken along a section line B-B in FIG. 4. FIGS. 7A to 7D and FIGS. 8A to 8C are cross section views for describing an example of the manufacturing method of the photoconductive antenna of the terahertz wave generating device shown in FIG. 1. Note that hereafter, in FIG. 1 and FIG. 4 to FIG. 8, the upper side will be described as "upper" and the lower side will be described as "lower."

As shown in FIG. 1, the terahertz wave generating device 1 has a light source device 3 that generates light pulses (pulsed light) which is excitation light, and a photoconductive antenna 2 for generating terahertz waves by irradiating light pulses generated by the light source device 3. A terahertz wave means an electromagnetic wave for which the frequency is 100 GHz or greater and 30 THz or less, and particularly an electromagnetic wave of 300 GHz or greater and 3 THz or less.

As shown in FIG. 4 to FIG. 6, with this embodiment, the light source device 3 has a light pulse generator 4 that generates light pulses, a first pulse compressor 5 that performs pulse compression on light pulses generated by the light pulse generator 4, a second pulse compressor 7 that performs pulse compression on light pulses for which pulse compression was done by the first pulse compressor 5, and an amplifier 6 that amplifies the light pulses.

The amplifier 6 can be provided at the front stage of the first pulse compressor 5, or between the first pulse compressor 5 and the second pulse compressor 7, but with the configuration in the drawing, the amplifier 6 is provided between the first pulse compressor 5 and the second pulse compressor 7. With this configuration, the light pulses which underwent pulse compression by the first pulse compressor 5 are amplified by the amplifier 6, and the light pulses amplified by the amplifier 6 undergo pulse compression by the second pulse compressor 7.

Also, the pulse width (half-value width) of the light pulses emitted from the light source device 3 is not particularly restricted, but is preferably 1 femtosecond or greater and 800 femtoseconds or less, and more preferably 10 femtoseconds or greater and 200 femtoseconds or less.

Also, the frequency of the light pulses emitted from the light source device 3 is set to the same or greater frequency corresponding to the band gap of the i type semiconductor layer 24 of the photoconductive antenna 2 described later.

Also, the light pulse generator 4 can use a so-called semiconductor laser such as a DBR laser, DFB laser, mode locked laser or the like, for example. The pulse width of the light pulses generated by this light pulse generator 4 is not particularly restricted, but is preferably 1 picosecond or greater and 100 picoseconds or less.

Also, the first pulse compressor 5 performs pulse compression based on saturable absorption. Specifically, the first pulse compressor 5 has a saturable absorber, and using that saturable absorber, light pulses are compressed and pulse width is decreased.

Also, the second pulse compressor 7 performs pulse compression based on group velocity dispersion compensation. Specifically, the second pulse compressor 7 has a group velocity dispersion compensation medium, and with this embodiment a coupled waveguide structure, and using that coupled waveguide structure, light pulses are compressed and pulse width is decreased.

Also, the light pulse generator 4 of the light source device 3, the first pulse compressor 5, the amplifier 6, and the second pulse compressor 7 are made into an integral unit, specifically, integrated on the same substrate.

In specific terms, the light source device 3 has a substrate 31 which is a semiconductor substrate, a cladding layer 32 which is provided on the substrate 31, an active layer 33 which is provided on the cladding layer 32, a waveguide structure processing etching stop layer 34 provided on the active layer 33, a cladding layer 35 provided on the waveguide structure processing etching stop layer 34, a contact layer 36 provided on the cladding layer 35, an insulation layer 37 provided on the waveguide structure processing etching stop layer 34, a cladding layer 32 side electrode 38 provided on the surface of the substrate 31, and cladding layer 35 side electrodes 391, 392, 393, 394, and 395 provided on the contact layer 36 and the insulation layer 37 surface. Also, a diffraction grating 30 is provided between the waveguide structure processing etching stop layer 34 of the light pulse generator 4 and the cladding layer 35. Note that the waveguide structure processing etching stop layer is not limited to being provided directly above the active layer, but can also be provided within the cladding layer, for example.

The structural materials of each part are not particularly restricted, but an example for the substrate 31 and the contact layer 36 is GaAs or the like. Also, an example for the cladding layers 32 and 35, the waveguide structure processing etching stop layer 34, and the diffraction grating 30 includes AlGaAs or the like. Also, for the active layer 33, an example is a structure using a quantum effect called a multiple quantum well or the like. In specific terms, an example of the active layer 33 is an item with a structure called a distributed index of refraction multiple quantum well structured with multiple quantum wells or the like made by alternately providing a plurality of well layers (GaAs well layers) and barrier layers (AlGaAs barrier layers) or the like.

With the constitution in the drawing, the waveguide of the light source device 3 is constituted from the cladding layer 32, the active layer 33, the waveguide structure processing etching stop layer 34, and the cladding layer 35. Also, the cladding layer 35 is provided in a shape corresponding to the waveguide, only on the top part of the waveguide. Also, the cladding layer 35 is formed by removal of the unnecessary parts by etching. Depending on the manufacturing method, it is possible to omit the waveguide structure processing etching stop layer 34.

Also, two each of the cladding layer 35 and the contact layer 36 are provided. One of the cladding layer 35 and the contact layer 36 constitute the light pulse generator 4, the first pulse compressor 5, the amplifier 6, and part of the second pulse compressor 7, and are provided sequentially, and the other cladding layer 35 and contact layer 36 constitute part of the second pulse compressor 7. Specifically, one pair of cladding layers 35 and one pair of contact layers 36 are provided on the second pulse compressor 7.

Also, the electrode 391 is provided so as to correspond to the cladding layer 35 of the light pulse generator 4, the electrode 392 is provided so as to correspond to the cladding layer 35 of the first pulse compressor 5, the electrode 393 is provided so as to correspond to the cladding layer 35 of the amplifier 6, and the electrodes 394 and 395 are provided so as to respectively correspond to the two cladding layers 35 of the second pulse compressor 7. The electrode 38 is a shared electrode of the light pulse generator 4, the first pulse compressor 5, the amplifier 6, and the second pulse compressor 7. Then, the pair of electrodes of the light pulse generator 4 is constituted by the electrode 38 and the electrode 391, the pair of electrodes of the first pulse compressor 5 is constituted by the electrode 38 and the electrode 392, the pair of electrodes of the amplifier 6 is constituted by the electrode 38 and the electrode 393, and the two pairs of electrodes of the second pulse compressor 7 are constituted by the electrode 38 and electrode 394 and the electrode 38 and electrode 395.

The overall shape of the light source device 3 is a rectangular solid with the constitution in the drawing, but naturally it is not restricted to this.

Also, the dimensions of the light source device 3 are not particularly restricted, but for example can be 1 mm or greater and 10 mm or less×0.5 mm or greater and 5 mm or less×0.1 mm or greater and 1 mm or less.

With the present invention, it also goes without saying that the constitution of the light source device is not restricted to the previously described constitution.

Next, the photoconductive antenna 2 will be described.

As shown in FIG. 1 and FIG. 2, the photoconductive antenna 2 has an n type semiconductor layer (first conductive region) 22, an i type semiconductor layer (semiconductor region) 24 for generating terahertz waves, a p type semiconductor layer (second conductive region) 23, and an electrode (first electrode) 28 and an electrode (second electrode) 29 constituting the pair of electrodes. The i type semiconductor layer 24 supports the n type semiconductor layer 22, the p type semiconductor layer 23, and the electrodes 28 and 29, and also acts as a substrate mainly to provide rigidity. Specifically, the n type semiconductor layer 22 and the p type semiconductor layer 23 are provided on the i type semiconductor layer 24, the electrode 28 is provided on the n type semiconductor layer 22, and the electrode 29 is provided on the p type semiconductor layer 23.

The i type semiconductor layer 24 does not have to also act as a substrate, and it is possible for the photoconductive antenna 2 to have a separate substrate and have the i type semiconductor layer provided only on the necessary sites.

Also, with the configuration in the drawing, the shape of the i type semiconductor layer 24 is rectangular when seen from the direction at which the light pulses are made incident. The shape of the i type semiconductor layer 24 is not restricted to being rectangular, and can also be a circle, an oval, or another polygon or the like such as a triangle, a pentagon, a hexagon or the like. Hereafter, "when seen from the direction at which the light pulses are made incident" or "when seen from the layer thickness direction of each semiconductor layer" is also called "the planar view."

This i type semiconductor layer 24 is constituted with a semiconductor material. The semiconductor material constituting this i type semiconductor layer 24 is preferably an intrinsic semiconductor, but may also include a small volume of a p type impurity or an n type impurity. In other words, the i type semiconductor layer 24 can be said to have a carrier density lower than the n type semiconductor layer 22 when it contains an n type impurity, and can be said to have a carrier density lower than the p type semiconductor layer 23 when it contains a p type impurity. It is preferable that even when the i type semiconductor layer 24 contains either an n type impurity or a p type impurity, the carrier density is lower than with the n type semiconductor layer 22 and the p type semiconductor layer 23.

In specific terms, the carrier density of the i type semiconductor layer 24 is preferably $1\times10^{18}$ cm$^3$ or less, more preferably $1\times10^{12}$/cm$^3$ or greater and $1\times10^{18}$/cm$^3$ or less, and even more preferably $1\times10^{12}$/cm$^3$ or greater and $1\times10^{16}$/cm$^3$ or less.

Also, the n type semiconductor layer 22 and the p type semiconductor layer 23 are arranged via a prescribed gap 25 on the i type semiconductor layer 24. With this configuration, in the top plan view, at least a portion of the i type semiconductor layer 24 is arranged at the gap 25 between the n type semiconductor layer 22 and the p type semiconductor layer 23. With this embodiment, a portion of the i type semiconductor layer 24 is arranged at that gap 25, and that gap 25 is filled (embedded) by a portion of the i type semiconductor layer 24. It is possible to generate higher intensity terahertz waves. With this terahertz wave generating device 1, the light pulses generated by the light source device 3 are made to be irradiated on the i type semiconductor layer 24 via the gap 25 and positioned within that gap 25. Therefore, the surface of the i type semiconductor layer 24 at the gap 25 (an interfacial surface with the air layer) constitutes the plane of incidence at which the light pulses are made incident.

In specific terms, the n type semiconductor layer 22 light pulse incidence side surface 221 (an interfacial surface with the electrode 28: a first interfacial surface in this embodiment), the p type semiconductor layer 23 light pulse incidence side surface 231 (an interfacial surface with the electrode 29: a first interfacial surface in this embodiment), and the light pulse incidence side surface 241 of the site positioned at the gap 25 of the i type semiconductor layer 24 (the interfacial surface) are arranged within the same plane (same surface) (i.e., the surface 241 is flush with the surface 221 and the surface 231). Then, the n type semiconductor layer 22 terahertz wave emission side surface 222 facing opposite the surface 221 (an interfacial surface with the i type semiconductor layer 24: a second interfacial surface in this embodiment) and the p type semiconductor layer 23 terahertz wave emission side surface 232 facing opposite the surface 231 (an interfacial surface with the i type semiconductor layer 24: a second interfacial surface in this embodiment) are arranged within the same plane. Specifically, the one interfacial surface of the n type semiconductor layer 22 and the one interfacial surface of the p type semiconductor layer 23 are arranged within the same surface, and the other interfacial surface of the n type semiconductor layer 22 and the other interfacial surface of the p type semiconductor layer 23 are arranged on the same side with respect to the previously described same plane (surface 241 at the gap 25 of the i type semiconductor layer 24). Hereafter, the light pulse incidence side surface is also called the "incidence side surface," and the terahertz wave emission side surface is also called the "emission side surface."

Also, the n type semiconductor layer 22 is constituted from a semiconductor material containing an n type (first conductive type) impurity. The carrier density (impurity concentration) of the n type semiconductor layer 22 is preferably $1\times10^{17}$/cm$^3$ or greater, more preferably $1\times10^{20}$/cm$^3$ or greater, and even more preferably $1\times10^{20}$/cm$^3$ or greater and $1\times10^{25}$/cm$^3$ or less. The n type impurity is not particularly restricted, but examples include Si, Ge, S, Se or the like.

Also, the p type semiconductor layer 23 is constituted by a semiconductor material containing a p type (second conductive type) impurity. The carrier density of the p type semiconductor layer 23 is preferably $1\times10^{17}$/cm$^3$ or greater, more preferably $1\times10^{20}$/cm$^3$ or greater, and even more preferably $1\times10^{20}$/cm$^3$ or greater and $1\times10^{25}$/cm$^3$ or less. This p type impurity is not particularly restricted, but examples include Zn, Mg, C or the like.

The n type semiconductor layer 22 and the p type semiconductor layer 23 can respectively be formed by, for example, doping a p type impurity in the i type semiconductor layer 24 using an ion implantation method, a diffusion method or the like. Specifically, the n type semiconductor layer 22 or the p type semiconductor layer 23 become areas in which n type or p type impurities are implanted at a designated depth along the surface of the i type semiconductor layer 24, so it is possible to form a layer shaped n type or p type semiconductor region.

The semiconductor material of the n type semiconductor layer 22, the p type semiconductor layer 23, and the i type semiconductor layer 24 is not particularly restricted, and it is possible to use various types of items, but it is preferable to use a III-V compound semiconductor. Also, the III-V compound semiconductor is not particularly restricted, and examples include GaAs, InP, InAs, InSb and the like.

With this kind of pin structure using the n type semiconductor layer 22, the i type semiconductor layer 24, and the p type semiconductor layer 23, the withstand voltage is improved, and this makes it possible to form a larger electric field, and thus, it is possible to generate higher intensity terahertz waves.

Also, the positional relationship of the n type semiconductor layer 22 and the p type semiconductor layer 23 is fixed without relying on the thickness of the i type semiconductor layer 24, so it is possible to make the electric field direction fixed, and with this configuration, it is possible to make the terahertz wave emission direction fixed.

The shape of the n type semiconductor layer 22 and the p type semiconductor layer 23 are respectively not particularly restricted, but with this embodiment, as shown in FIG. 3A, the n type semiconductor layer 22 is constituted by a band shaped part 224 in a band shape, and a projecting part 223 provided midway in the band shaped part 224, specifically, in its middle part, and projecting to the p type semiconductor layer 23 side. Also, as shown in FIG. 3B, the projecting part 223 may also be provided at the end part of the band shaped part 224. With the constitution in the drawing, with the planar view, the shape of the projecting part 223 is a rectangular shape. The shape of the projecting part 223 is not restricted to being rectangular, and can also be a circle, an oval, or another polygon or the like such as a triangle, a pentagon, a hexagon or the like.

Also, with this embodiment, the p type semiconductor layer 23 has a shape that is the reverse of the n type semiconductor layer 22. Specifically, as shown in FIG. 3A, the p type semiconductor layer 23 is constituted by a band shaped part 234 in a band shape, and a projecting part 233 provided midway in the band shaped part 234, specifically, in its middle part, and projecting to the n type semiconductor layer 22 side. Also, as shown in FIG. 3B, the projecting part 233 may also be provided on the end part of the band shaped part 234. With the constitution in the drawing, with the planar view, the shape of the projecting part 233 is a rectangular shape. The shape of the projecting part 233 is not restricted to being rectangular, and can also be a circle, an oval, or another polygon or the like such as a triangle, a pentagon, a hexagon or the like.

The n type semiconductor layer 22 and the p type semiconductor layer 23 are arranged such that the band shaped part 224 of the n type semiconductor layer 22 and the band shaped part 234 of the p type semiconductor layer 23 are parallel.

Also, the thickness d1 of the n type semiconductor layer 22 and the thickness d2 of the p type semiconductor layer 23 are not particularly restricted, and are set as appropriate according to various conditions, but are preferably 10 nm or greater and 1 μm or less. The thickness d1 of the n type semiconductor layer 22 and the thickness d2 of the p type semiconductor layer 23 may be the same or may be different, but with this embodiment, they are set to be the same.

Also, the distance (gap distance) d of the gap 25 between the n type semiconductor layer 22 and the p type semiconductor layer 23 is not particularly restricted, and is set as appropriate according to various conditions, but is preferably 1 μm or greater and 10 μm or less.

Also, the width w1 of the projecting part 223 of the n type semiconductor layer 22 and the width w2 of the projecting part 233 of the p type semiconductor layer 23 are not particularly restricted, and are set as appropriate according to various conditions, but are preferably 1 μm or greater and 10 μm or less. The width w1 of the projecting part 223 of the n type semiconductor layer 22 and the width w2 of the projecting part 233 of the p type semiconductor layer 23 may be the same, or may be different, but with this embodiment, they are set to be the same.

Also, the electrode 28 is provided on the n type semiconductor layer 22. Specifically, the electrode 28 is in contact with the n type semiconductor layer, and is electrically connected to that n type semiconductor layer 22.

Also, the electrode 29 is provided on the p type semiconductor layer 23. Specifically, the electrode 29 is in contact with the p type semiconductor layer 23, and is electrically connected to that p type semiconductor layer 23.

Also, the respective shapes of the electrodes 28 and 29 are not particularly restricted, but with this embodiment, the electrode 28 and the n type semiconductor layer 22 have the same shape. With this configuration, it is possible to lower the contact resistance between the electrode 28 and the n type semiconductor layer 22, and to reduce the power consumption. In specific terms, the electrode 28 has a band shape, and is constituted by a band shaped part 282 that functions as wiring, and a projecting part 281 provided midway in the band shaped part 282, specifically, at the middle part, that projects to the electrode 29 side. With the constitution in the drawing, with the planar view, the shape of the projecting part 281 is a rectangle. The shape of the projecting part 281 is not restricted to being rectangular, and can also be a circle, an oval, or another polygon or the like such as a triangle, a pentagon, a hexagon or the like.

With this embodiment, the electrode 29 and the p type semiconductor layer 23 have the same shape. With this configuration, it is possible to lower the contact resistance between the electrode 29 and the p type semiconductor layer 23, and to reduce the power consumption. Specifically, the electrode 29 has a shape that is the reverse of the n type semiconductor layer 22. In specific terms, the electrode 29 has a band shape, and is constituted by a band shaped part 292 that functions as wiring, and a projecting part 291 provided midway in the band shaped part 292, specifically, at the middle part, that projects to the electrode 28 side. With the constitution in the drawing, in the top plan view, the shape of the projecting part 291 is a rectangle. The shape of the projecting part 291 is not restricted to being rectangular, and can also be a circle, an oval, or another polygon or the like such as a triangle, a pentagon, a hexagon or the like.

The electrode 28 and the electrode 29 are arranged such that the band shaped part 282 of the electrode 28 and the band shaped part 292 of the electrode 29 are parallel.

A power supply device 18 is electrically connected to the electrodes 28 and 29 respectively via a pad, conducting wire, connector or the like (not illustrated), and direct current voltage is applied between the electrode 28 and the electrode 29 so that the electrode 28 side is positive.

Next, an example of the manufacturing method of the photoconductive antenna 2 of the terahertz wave generating device 1 will be described.

Figure 7A:
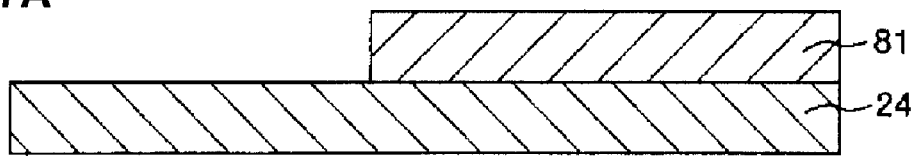
FIGS. 7A to 7D are cross section diagrams for describing one example of the manufacturing method of the photoconductive antenna of the terahertz wave generating device shown in FIG. 1.

First, as shown in FIG. 7A, a resist layer 81 is formed on the top surface of the i type semiconductor layer 24, and the resist layer 81 is removed at the sites at which the p type semiconductor layer 23 is formed on the top surface of the i type semiconductor layer 24.

Figure 7B:
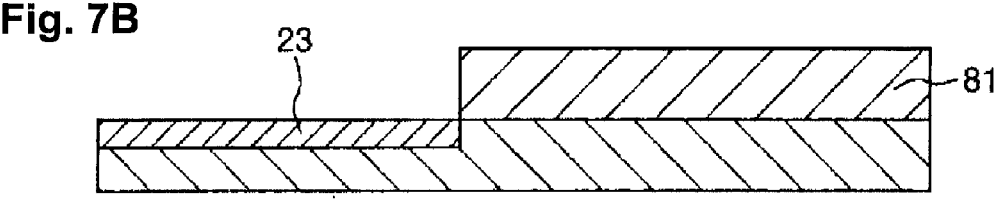

Next, as shown in FIG. 7B, a p type impurity is doped in the i type semiconductor layer 24 using an ion implantation method, diffusion method or the like, for example. With this configuration, the p type semiconductor layer 23 is formed. Then, the resist layer 81 is removed.

Figure 7C:
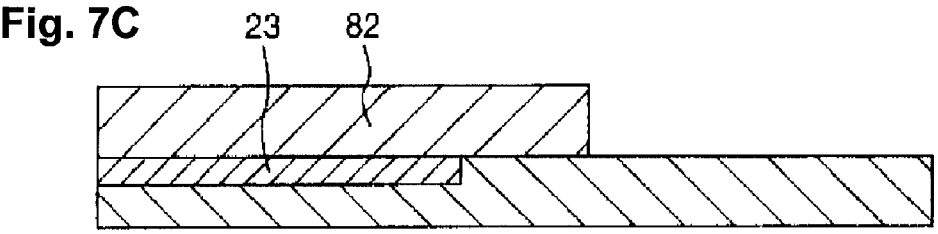

Next, as shown in FIG. 7C, a resist layer 82 is formed on the i type semiconductor layer 24 and the p type semiconductor layer 23 top surface, and the resist layer 82 is removed at the sites at which the n type semiconductor layer 22 is formed on the top surface of the i type semiconductor layer 24.

Figure 7D:
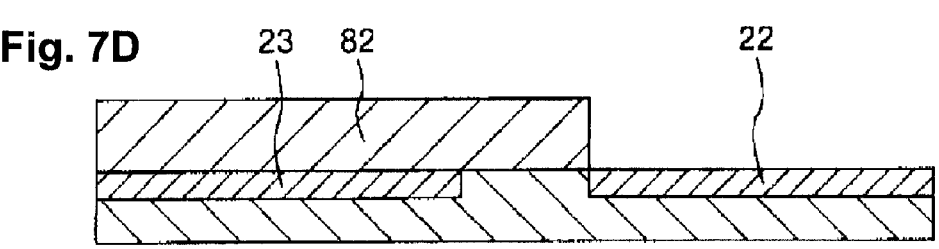

Next, as shown in FIG. 7D, an n type impurity is doped in the i type semiconductor layer 24 using an ion implantation method, diffusion method or the like, for example. With this configuration, the n type semiconductor layer 22 is formed. Then, the resist layer 82 is removed.

Figure 8A:
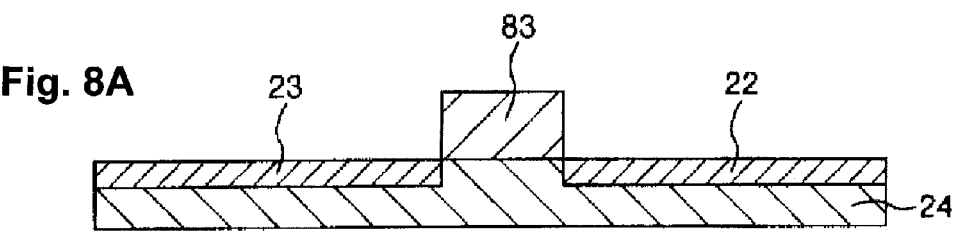
FIGS. 8A to 8C are cross section diagrams for describing one example of the manufacturing method of the photoconductive antenna of the terahertz wave generating device shown in FIG. 1.

Next, as shown in FIG. 8A, a resist layer 83 is formed on the i type semiconductor layer 24, the p type semiconductor layer 23, and the n type semiconductor layer 22 top surface, the resist layer 83 of the top surface of the p type semiconductor layer 23 and the n type semiconductor layer 22 is removed, and the resist layer 83 remains only on the top surface of the i type semiconductor layer 24.

Figure 8B:
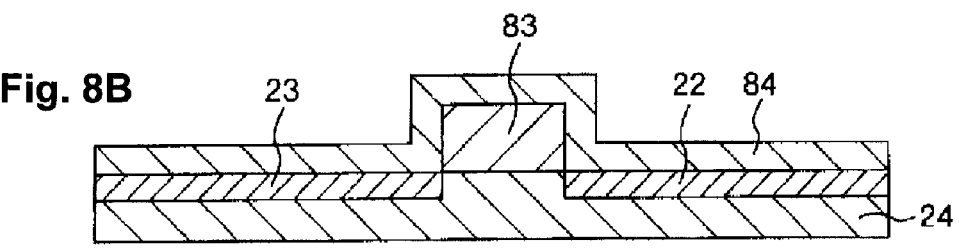

Next, as shown in FIG. 8B, a metal layer 84 is formed on the p type semiconductor layer 23, the n type semiconductor layer 22, and the resist layer 83 top surface. The constitutional material of this metal layer 84 is the same as the constitutional material of the electrodes 28 and 29.

Figure 8C:
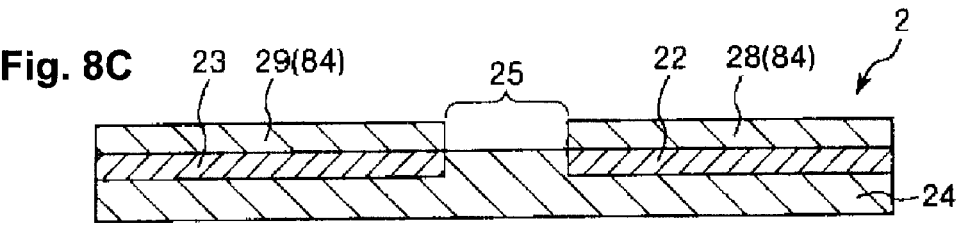

Next, as shown in FIG. 8C, the resist layer 83 is removed for each metal layer 84 formed on the top surface thereof. With this configuration, the electrodes 28 and 29 are formed. By doing as described above, the photoconductive antenna 2 is manufactured.

Next, the operation of the terahertz wave generating device 1 will be described.

With the terahertz wave generating device 1, first, light pulses are generated by the light pulse generator 4 of the light source device 3. The pulse width of the light pulses generated by the light pulse generator 4 is larger than the target pulse width. The light pulses generated by the light pulse generator 4 pass through the waveguide, and pass through the first pulse compressor 5, the amplifier 6, and the second pulse compressor 7 sequentially in that order.

First, at the first pulse compressor 5, pulse compression based on saturable absorption is performed on the light pulses, and the pulse width of the light pulses is decreased. Next, at the amplifier 6, the light pulses are amplified. Finally, at the second pulse compressor 7, pulse compression based on group velocity dispersion compensation is performed on the light pulses, and the pulse width of the light pulses is decreased. In this way, light pulses of the target pulse width are generated, and are emitted from the second pulse compressor 7.

The light pulses emitted from the light source device 3 are irradiated on the surface of the i type semiconductor layer 24 at the gap 25 of the photoconductive antenna 2, and terahertz waves are generated by that i type semiconductor layer 24. These terahertz waves are emitted from the bottom surface of the i type semiconductor layer 24, specifically, from the emission plane.

As described above, with this terahertz wave generating device 1, with the pin structure, the withstand voltage is increased, and with this configuration, it is possible to form a larger electric field, and as a result, it is possible to generate higher intensity terahertz waves.

Also, the positional relationship of the n type semiconductor layer 22 and the p type semiconductor layer 23 is fixed without depending on the thickness of the i type semiconductor layer 24, so it is possible to fix the direction of the electric field, and with this configuration, it is possible to fix the emission direction of the terahertz waves.

Also, the light source device 3 has the first pulse compressor 5, the amplifier 6, and the second pulse compressor 7, so it is possible to make the light source device 3 more compact, and thus the terahertz wave generating device 1 more compact, and it is also possible to generate light pulses with a desired wave height and desired width, and with this configuration, it is possible to reliably generate the desired terahertz waves.

With this embodiment, in the top plan view, the electrode 28 and the n type semiconductor layer 22 have the same shape, but it is also acceptable for the electrode 28 and the n type semiconductor layer 22 to not have the same shape.

Also, with this embodiment, in the top plan view, the electrode 29 and the p type semiconductor layer 23 have the same shape, but it is also acceptable for the electrode 29 and the p type semiconductor layer 23 to not have the same shape.

In specific terms, for example, it is also possible to omit the band shaped part 224 of the n type semiconductor layer 22, and to constitute the n type semiconductor layer 22 using the projecting part 223. Similarly, it is also possible to omit the band shaped part 234 of the p type semiconductor layer 23, and to constitute the p type semiconductor layer 23 using the projecting part 233.

Also, for example, it is possible to omit the projecting part 281 of the electrode 28, and to constitute the electrode 28 using the band shaped part 282. Similarly, it is possible to omit the projecting part 291 of the electrode 29, and to constitute the electrode 29 using the band shaped part 292.

Also, for example, it is possible to omit the band shaped part 224 of the n type semiconductor layer 22 and constitute the n type semiconductor layer 22 using the projecting part 223, and to omit the projecting part 281 of the electrode 28 and constitute the electrode 28 using the band shaped part 282. Similarly, it is possible to omit the band shaped part 234 of the p type semiconductor layer 23 and constitute the p type semiconductor layer 23 using the projecting part 233, and to omit the projecting part 291 of the electrode 29 and constitute the electrode 29 using the band shaped part 292.

Second Embodiment

Figure 9:
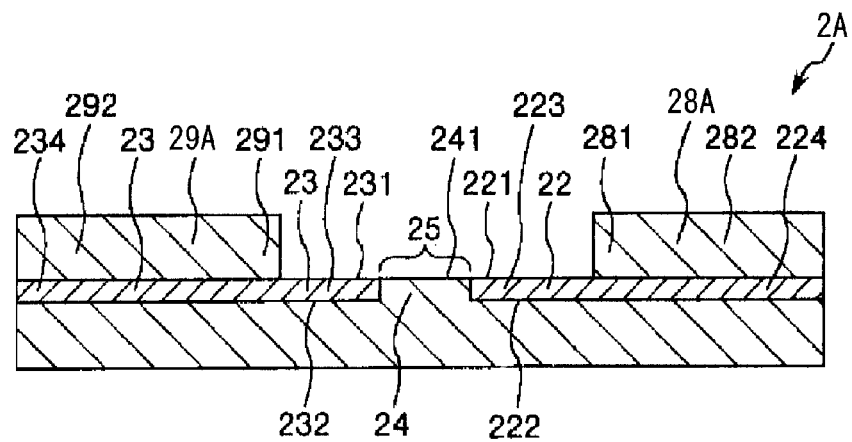
FIG. 9 is a cross section diagram of a photoconductive antenna according to a second embodiment of the present invention.

FIG. 9 is a cross section diagram showing a photoconductive antenna 2A according to the second embodiment of the present invention. Hereafter, in FIG. 9, the upper side will be described as "upper" and the lower side will be described as "lower."

Hereafter, the description of the second embodiment will focus on the differences from the first embodiment, and a description will be omitted for items that are the same.

As shown in FIG. 9, with the photoconductive antenna 2A of the second embodiment, the electrode 28A and the n type semiconductor layer 22 have different shapes, and the electrode 29A and the p type semiconductor layer 23 have different shapes.

Specifically, the length of the projecting part 223 of the n type semiconductor layer 22 in the lateral direction of FIG. 9 is set to be longer than the length of the projecting part 281 of the electrode 28A in the lateral direction of FIG. 9, and the length of the projecting part 233 of the p type semiconductor layer 23 in the lateral direction of FIG. 9 is set to be longer than the length of the projecting part 291 of the electrode 29A in the lateral direction of FIG. 9. With this configuration, it is possible to more reliably prevent the occurrence of leaked current at the gap 25 between the n type semiconductor layer 22 and the p type semiconductor layer 23.

With this photoconductive antenna 2A, the same effects are obtained as with the previously described first embodiment.

This second embodiment can also be applied to the third and fourth embodiments described later.

Third Embodiment

Figure 10:
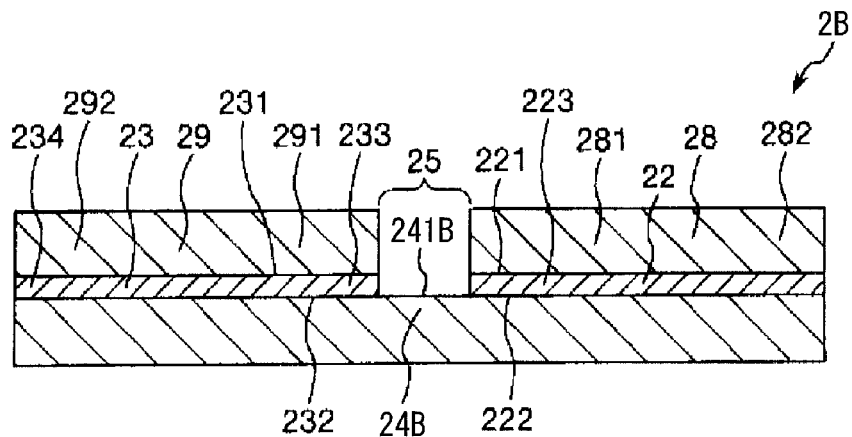
FIG. 10 is a cross section diagram of a photoconductive antenna according to a third embodiment of the present invention.

FIG. 10 is a cross section diagram showing a photoconductive antenna 2B according to a third embodiment of the present invention. Hereafter, in FIG. 10, the upper side will be described as "upper" and the lower side will be described as "lower."

Hereafter, the description of the third embodiment will focus on the differences from the first embodiment, and a description will be omitted for items that are the same.

As shown in FIG. 10, with the photoconductive antenna 2B of the third embodiment, the n type semiconductor layer 22 terahertz wave emission side surface 222 (an interfacial surface with the i type semiconductor layer 24B: a first interfacial surface in this embodiment), the p type semiconductor layer 23 terahertz wave emission side surface 232 (an interfacial surface with the i type semiconductor layer 24B: a first interfacial surface in this embodiment), and the i type semiconductor layer 24B incidence side surface 241B (an interfacial surface) are arranged within the same plane (i.e., the surface 241B is flush with the surface 222 and the surface 232). Then, the n type semiconductor layer 22 incidence side surface 221 (an interfacial surface with the electrode 28: a second interfacial surface in this embodiment) and the p type semiconductor layer 23 incidence side surface 231 (an interfacial surface with the electrode 29: a second interfacial surface in this embodiment) are arranged within the same plane.

The n type semiconductor layer 22 and the p type semiconductor layer 23 can respectively be formed on the i type semiconductor layer 24B using an epitaxial method or the like, for example. Specifically, for the n type semiconductor layer 22 or the p type semiconductor layer 23 to be formed at a designated thickness along the surface of the i type semiconductor layer 24B, it is possible to form a layer shaped n type or p type semiconductor region.

With this photoconductive antenna 2B, the same effects are obtained as with the previously described first embodiment.

This third embodiment can also be applied to the fourth embodiment described later.

Fourth Embodiment

Figure 11:
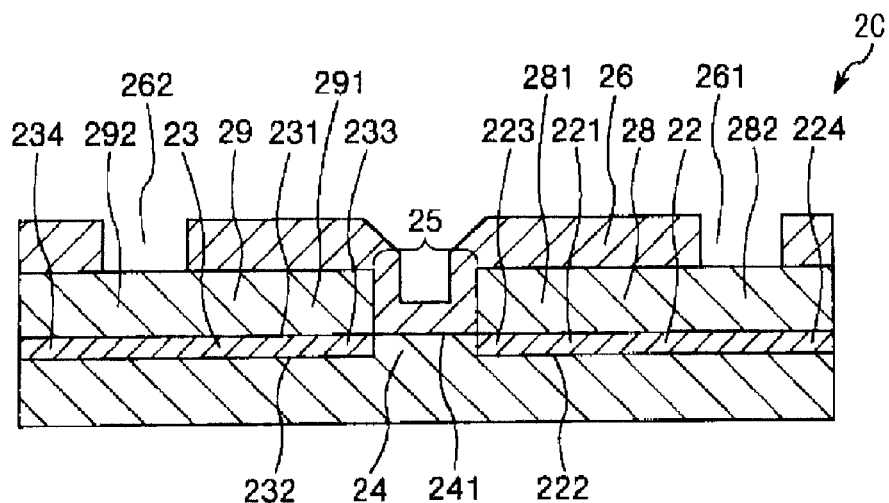
FIG. 11 is a cross section diagram of a photoconductive antenna according to a fourth embodiment of the present invention.
Figure 12A:
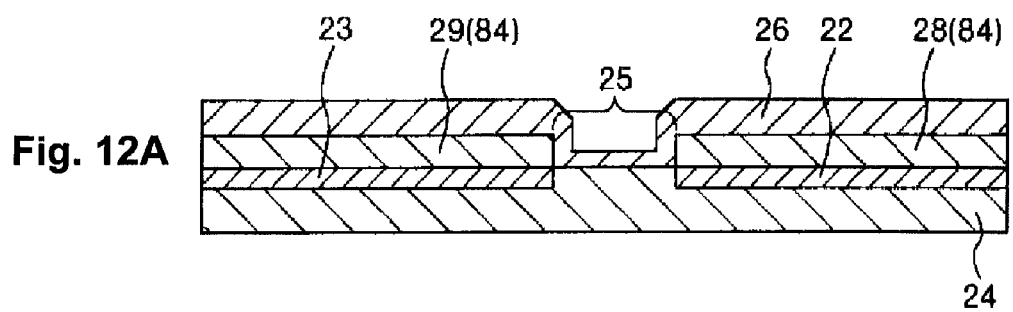
FIGS. 12A to 12C are cross section diagrams for describing an example of the manufacturing method of the photoconductive antenna shown in FIG. 11.
Figure 12B:
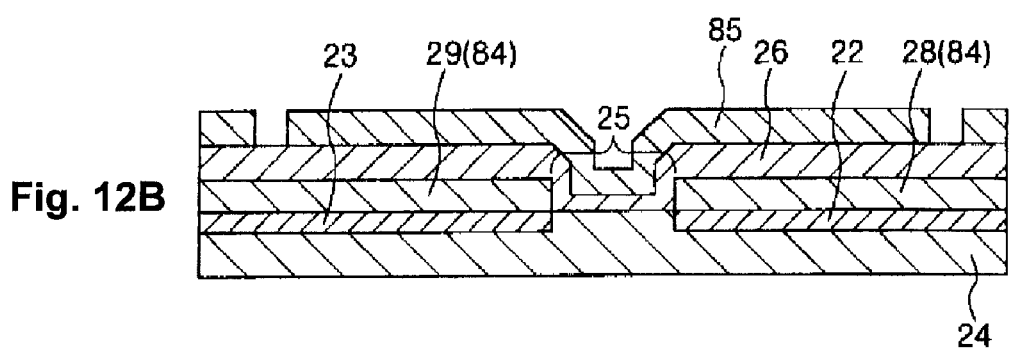
Figure 12C:
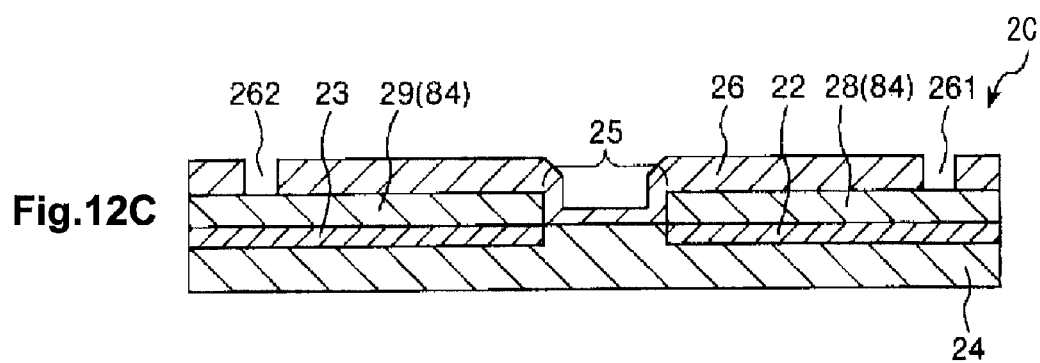

FIG. 11 is a cross section diagram showing a photoconductive antenna 2C according to a fourth embodiment of the present invention. FIGS. 12A to 12C are cross section diagrams for describing an example of the manufacturing method of the photoconductive antenna 2C shown in FIG. 11. Hereafter, in FIG. 11 and FIG. 12, the upper side will be described as "upper" and the lower side will be described as "lower."

Hereafter, the description of the fourth embodiment will focus on the differences from the first embodiment, and a description will be omitted for items that are the same.

As shown in FIG. 11, with the photoconductive antenna 2C of the fourth embodiment, on the i type semiconductor layer 24 at the gap 25 between the electrodes 28 and 29, the n type semiconductor layer 22, and the p type semiconductor layer 23, an insulation layer (insulation region) 26 covering these is provided.

Also, a void part 261 is provided on the insulation layer 26 on the band shaped part 282 of the electrode 28, exposing a portion of the band shaped part 282, and with this configuration, a conductive pad part is formed. Similarly, a void part 262 is provided on the insulation layer 26 on the band shaped part 292 of the electrode 29, exposing a portion of the band shaped part 292, and with this configuration, a conductive pad part is formed.

With this insulation layer 26, it is possible to more reliably prevent the occurrence of leaked current at the gap 25. Also, it is possible to prevent corrosion or the like of the i type semiconductor layer 24.

The constitutional material of the insulation layer 26 is not particularly restricted as long as it is an insulating material, and examples include metal compounds such as $SiO_2$, SiN, SiON, $Al_2O_3$ and the like.

Next, an example of the manufacturing method of the photoconductive antenna 2C will be described.

As shown in FIG. 8C, the resist layer 83 is removed for each the metal layer 84 formed on the top surface thereof, and up to the point of forming the electrodes 28 and 29 is the same as with the previously described first embodiment, so the description of the manufacturing method up to that point will be omitted.

Next, as shown in FIG. 12A, the insulation layer 26 is formed on the entire top surface of the i type semiconductor layer 24 at the gap 25 between the electrodes 28 and 29, the n type semiconductor layer 22, and the p type semiconductor layer 23.

Next, as shown in FIG. 12B, a resist layer 85 is formed on the top surface of the insulation layer 26, and the resist layer 85 is removed at the site at which the void parts 261 and 262 are formed on the top surface of the insulation layer 26.

Next, as shown in FIG. 12C, with the resist layer 85 as a mask, etching is implemented from the top surface side. Then, the resist layer 85 is removed. Working in this way, the void part 261 is formed on the insulation layer 26 on the band shaped part 282 of the electrode 28, and the void part 262 is formed on the insulation layer 26 on the band shaped part 292 of the electrode 29. Working as described above, the photoconductive antenna 2C is manufactured.

With this photoconductive antenna 2C, the same effects as those of the first embodiment described above are obtained.

With this embodiment, the insulation layer 26 is provided on the entire top of the i type semiconductor layer 24 at the gap 25 between the electrodes 28 and 29, the n type semiconductor layer 22, and the p type semiconductor layer 23, except for the conductive pad part of the electrodes 28 and 29, but the invention is not restricted to this, and it is also acceptable to provide it on at least a portion of the i type semiconductor layer 24 in the gap 25.

Embodiment of Imaging Device

Figure 13:
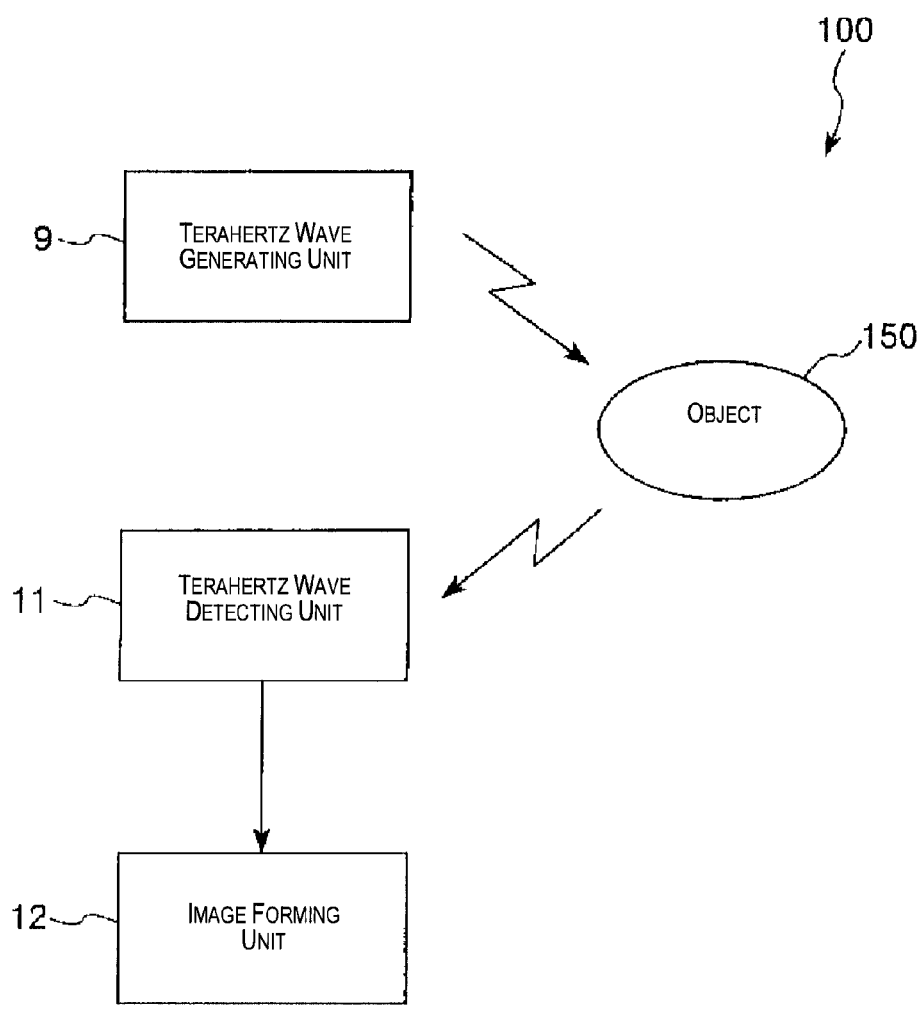
FIG. 13 is a block diagram showing an embodiment of the imaging device of the present invention.
Figure 14:
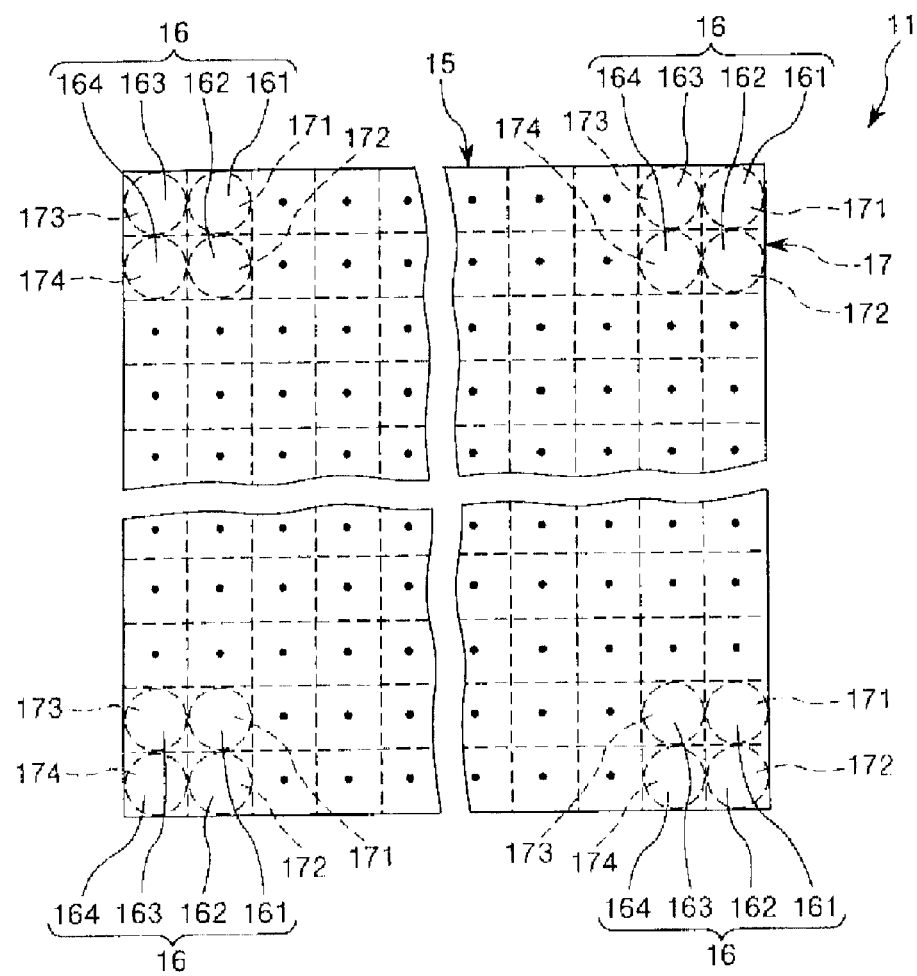
FIG. 14 is a top plan view showing the terahertz wave detecting unit of the imaging device shown in FIG. 13.
Figure 15:
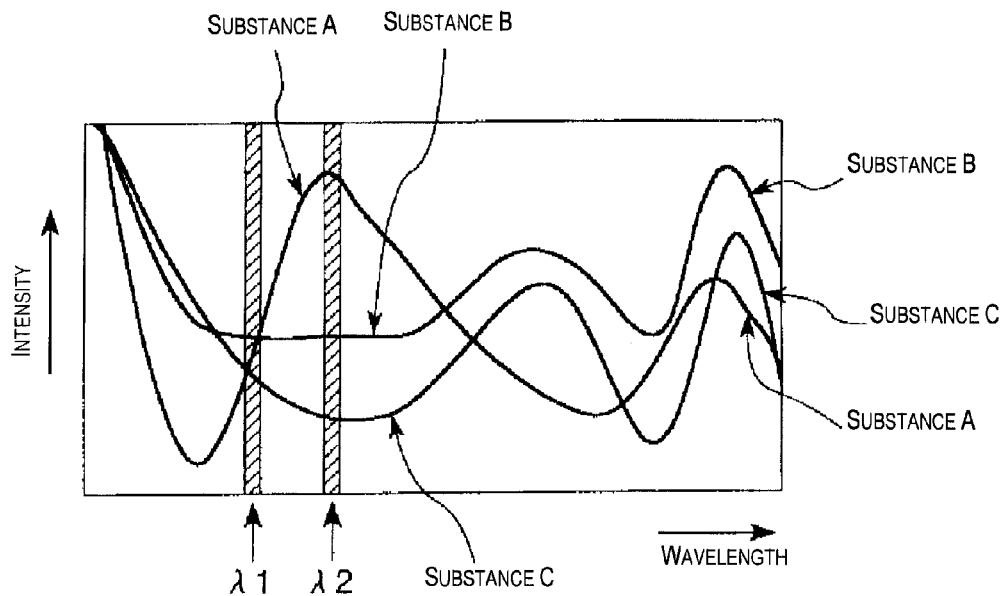
FIG. 15 is a graph showing the spectrum in the terahertz band of the object.
Figure 16:
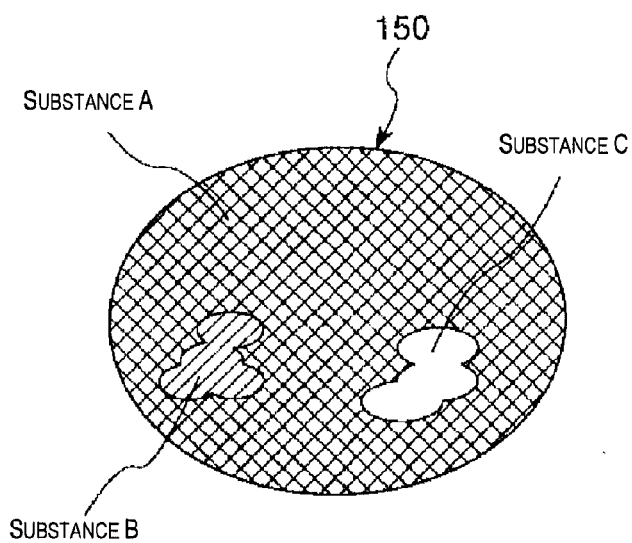
FIG. 16 is a drawing of the image showing the distribution of substances A, B, and C of the object.

FIG. 13 is a block diagram showing an embodiment of the imaging device of the present invention. FIG. 14 is a top plan view showing the terahertz wave detecting unit of the imaging device shown in FIG. 13. FIG. 15 is a graph showing the spectrum of the terahertz band of the object. FIG. 16 is a drawing of an image showing the distribution of the substances A, B, and C of the object.

As shown in FIG. 13, the imaging device 100 is equipped with a terahertz wave generating unit 9, a terahertz wave detecting unit 11 for detecting terahertz waves emitted from the terahertz wave generating unit 9 and passed through or reflected by the object 150, and an image forming unit 12 that generates an image of the object 150, specifically, image data, based on the detection results of the terahertz wave detecting unit 11. The configuration of the terahertz wave generating unit 9 is the same as the previously noted terahertz wave generating device 1, so a description will be omitted here.

Also, as the terahertz wave detecting unit 11, an item is used that is equipped with a filter 15 that transmits terahertz waves of target wavelengths, and a detection unit 17 that detects the terahertz waves of the target wavelengths transmitted by the filter 15. Also, as the detection unit 17, for example, an item is used that converts terahertz waves to heat and detects it, specifically, an item that converts terahertz waves to heat, and detects the energy (intensity) of the terahertz waves. As this kind of detection unit, examples include pyroelectric sensors, bolometers and the like. Naturally, the terahertz wave detecting unit 11 is not restricted to an item of this constitution.

Also, the filter 15 has a plurality of pixels (unit filter units) 16 arranged two dimensionally. Specifically, the pixels 16 are arranged in matrix form.

Also, the pixels 16 have a plurality of fields that transmit terahertz waves of mutually different wavelengths, specifically, a plurality of fields that have mutually different transmitted terahertz wavelengths (hereafter also called "transmission wavelengths"). With the constitution in the drawing, each pixel 16 has a first field 161, a second field 162, a third field 163, and a fourth field 164.

Also, the detection unit 17 has a first unit detecting unit 171, a second unit detecting unit 172, a third unit detecting unit 173, and a fourth unit detecting unit 174 provided respectively corresponding to the first field 161, second field 162, third field 163, and fourth field 164 of each pixel 16 of the filter 15. Each first unit detecting unit 171, second unit detecting unit 172, third unit detecting unit 173, and fourth unit detecting unit 174 respectively convert to heat and detect terahertz waves that were transmitted through the first field 161, the second field 162, the third field 163, and the fourth field 164 of each pixel 16. As a result, at each respective pixel 16, it is possible to reliably detect the terahertz waves of four target wavelengths.

Next, a use example of the imaging device 100 will be described.

First, the object 150 that is the subject of spectral imaging is constituted by three substances A, B, and C. The imaging device 100 performs spectral imaging of this object 150. Also, here, as an example, the terahertz wave detecting unit 11 detects terahertz waves reflected by the object 150.

With each pixel 16 of the filter 15 of the terahertz wave detecting unit 11, a first field 161 and a second field 162 are used.

Also, when the transmission wavelength of the first field 161 is $\lambda 1$ and the transmission wavelength of the second field 162 is $\lambda 2$, and the intensity of the wavelength $\lambda 1$ component of the terahertz wave reflected by the object 150 is $\alpha 1$ and the intensity of the transmission wavelength $\lambda 2$ component is $\alpha 2$, the transmission wavelength $\lambda 1$ of the first field 161 and the transmission wavelength $\lambda 2$ of the second field 162 are set so that the difference ($\alpha 2 - \alpha 1$) between the intensity $\alpha 2$ and intensity $\alpha 1$ can be clearly mutually distinguished for the substance A, substance B, and substance C.

As shown in FIG. 15, with substance A, the difference between the intensity $\alpha 2$ of the wavelength $\lambda 2$ component of the terahertz waves reflected by the object 150 and the intensity $\alpha 1$ of the wavelength $\lambda 1$ component ($\alpha 2 - \alpha 1$) is a positive value.

With substance B, the difference between intensity $\alpha 2$ and intensity $\alpha 1$ ($\alpha 2 - \alpha 1$) is zero.

With substance C, the difference between intensity $\alpha 2$ and intensity $\alpha 1$ ($\alpha 2 - \alpha 1$) is a negative value.

With the imaging device 100, when performing spectral imaging of the object 150, first, terahertz waves are generated by the terahertz wave generating unit 9, and those terahertz waves are irradiated on the object 150. Then, the terahertz wave detecting unit 11 detects the terahertz waves reflected by the object 150 as $\alpha 1$ and $\alpha 2$. These detection results are sent to the image forming unit 12. The detection of irradiation of terahertz waves on the object 150 and terahertz waves reflected by the object 150 is performed for the overall object 150.

The image forming unit 12 finds the difference ($\alpha 2 - \alpha 1$) between the intensity $\alpha 2$ of the wavelength $\lambda 2$ component of the terahertz waves transmitted through the second field 162 of the filter 15 and the intensity $\alpha 1$ of the wavelength $\lambda 1$ component of the terahertz waves transmitted through the first field 161 based on the detection results. Then, of the object 150, sites for which the difference is a positive value are determined and specified as being substance A, sites for which the difference is zero as substance B, and sites for which the difference is a negative value as substance C.

As shown in FIG. 16, the image forming unit 12 creates image data of an image showing the distribution of the substances A, B and C of the object 150. This image data is sent to a monitor (not illustrated) from the image forming unit 12, and an image showing the distribution of the substance A, substance B, and substance C of the object 150 is displayed on the monitor. In this case, for example, color coded display is done so that the field in which substance A of the object 150 is distributed is shown as black, the field in which substance B is distributed is shown as gray, and the field in which substance C is distributed is shown as white. With this imaging device 100, as described above, it is possible to identify each substance constituting the object 150 and to simultaneously perform distribution measurement of each substance.

The application of the imaging device 100 is not limited to the item described above, and for example, it is possible to irradiate terahertz waves on a person, to detect terahertz waves transmitted or reflected by that person, and by performing processing at the image forming unit 12, it is possible to determine whether that person is holding a gun, knife, illegal drugs or the like.

Embodiment of Measuring Device

Figure 17:
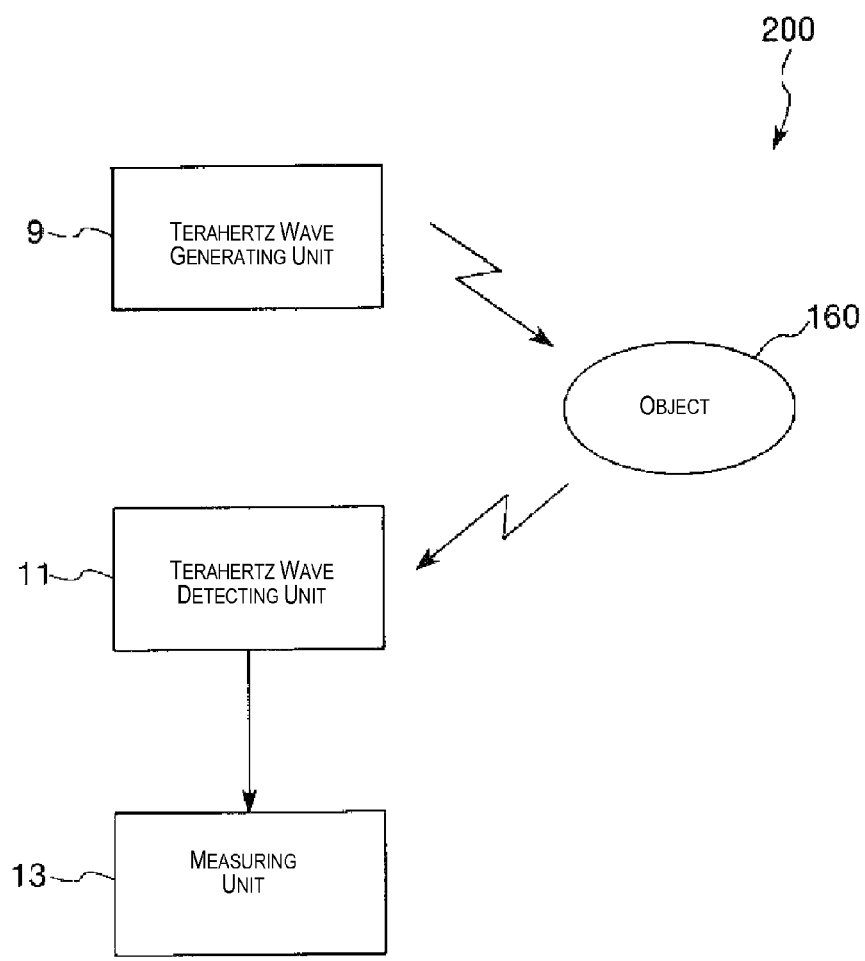
FIG. 17 is a block diagram showing an embodiment of the measuring device of the present invention.

FIG. 17 is a block diagram showing an embodiment of the measuring device of the present invention.

Following, the description of the embodiment of the measuring device will focus on the differences from the previously described embodiment of the imaging device, the same items will be given the same code numbers, and a detailed description of those will be omitted.

As shown in FIG. 17, the measuring device 200 is equipped with a terahertz wave generating unit 9 for generating terahertz waves, a terahertz wave detecting unit 11 for detecting terahertz waves emitted from the terahertz wave generating unit 9 and transmitted through or reflected by the object 160, and a measuring unit 13 for measuring the object 160 based on the detection results of the terahertz wave detecting unit 11.

Next, a use example of the measuring device 200 will be described.

With the measuring device 200, when performing spectroscopic measurement of the object 160, first, terahertz waves are generated by the terahertz wave generating unit 9, and those terahertz waves are irradiated on the object 160. Then, the terahertz waves transmitted by or reflected by the object 160 are detected by the terahertz wave detecting unit 11. These detection results are sent to the measuring unit 13. Irradiation of the terahertz waves on the object 160 and detection of the terahertz waves transmitted by or reflected by the object 160 are performed for the overall object 160.

With the measuring unit 13, from the detection results, the respective intensities of the terahertz waves that were transmitted through the first field 161, the second field 162, the third field 163, and the fourth field 164 of the filter 15 are found out, and analysis or the like of the object 160 components and their distribution is performed.

Embodiment of Camera

Figure 18:
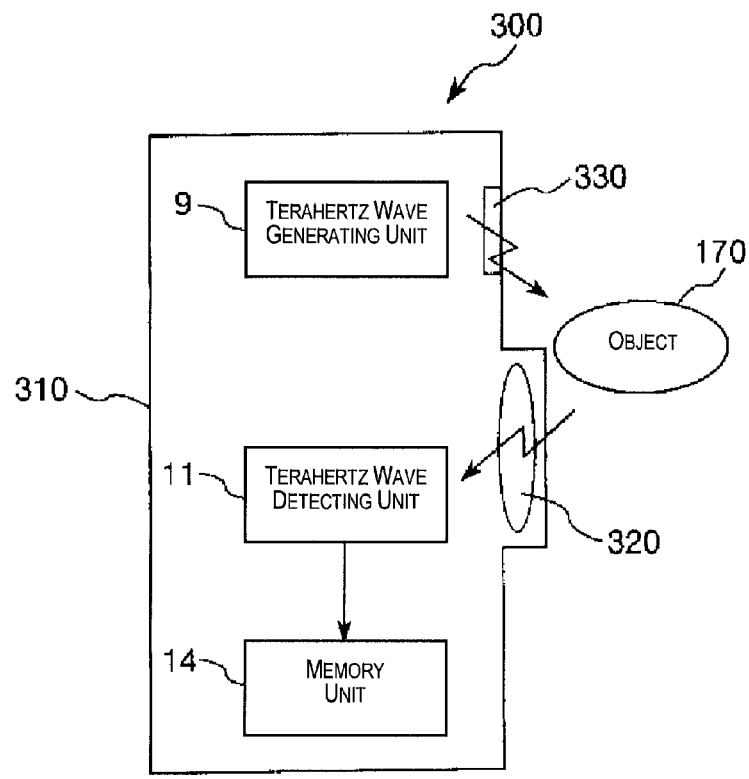
FIG. 18 is a block diagram showing an embodiment of the camera of the present invention.

FIG. 18 is a block diagram showing the embodiment of the camera of the present invention. Also, FIG. 19 shows a schematic perspective view showing an embodiment of the camera of the present invention.

Following, the description of the embodiment of the camera will focus on the differences from the previously described embodiment of the image device, the same items are given the same code numbers as in the previously described embodiments, and a detailed description of those will be omitted.

Figure 19:
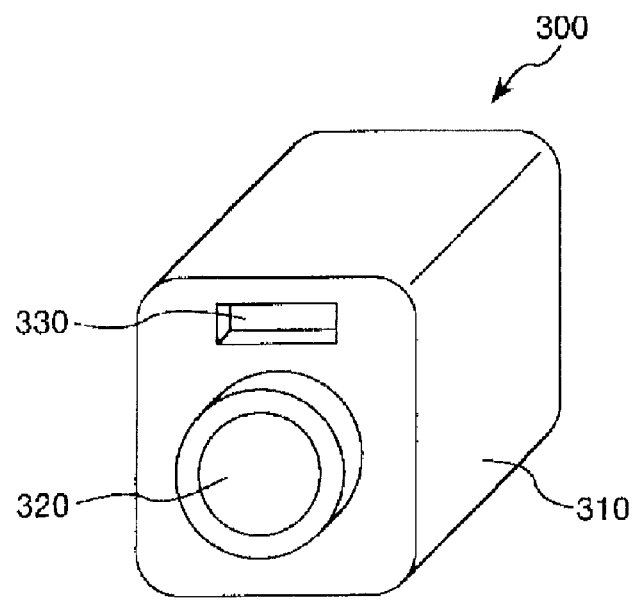
FIG. 19 is a schematic perspective view showing an embodiment of the camera of the present invention.

As shown in FIG. 18 and FIG. 19, the camera 300 is equipped with a terahertz wave generating unit 9 for generating terahertz waves, a terahertz wave detecting unit 11 for detecting terahertz waves emitted from the terahertz wave generating unit 9 and reflected by the object 170, and a memory unit 14. Then, each of these parts is housed in a case 310 of the camera 300. Also, the camera 300 is equipped with a lens (optical system) 320 for converging (imaging) the terahertz waves reflected by the object 170 on the terahertz wave detecting unit 11, and a window part 330 for emitting to outside the case 310 the terahertz waves generated by the terahertz wave generating unit 9. The lens 320 and the window part 330 are constituted by members using silicon, quartz, polyethylene or the like that transmit or refract terahertz waves. The window part 330 can also be constituted with an aperture simply provided as a slit.

Next, a use example of the camera 300 will be described.

With the camera 300, when taking an image of the object 170, first, terahertz waves are generated by the terahertz wave generating unit 9, and those terahertz waves are irradiated on the object 170. Then, the terahertz waves reflected by the object 170 are converged (imaged) by the lens 320 to the terahertz wave detecting unit 11 and detected. The detection results are sent to and stored in the memory unit 14. Detection of irradiation of the terahertz waves on the object 170 and of the terahertz waves reflected by the object 170 is performed on the overall object 170. The detection results can also be sent to an external device such as a personal computer or the like, for example. With the personal computer, it is possible to perform various processes based on the detection results.

Above, the photoconductive antenna, the terahertz wave generating device, the camera, the imaging device, and the measuring device of the present invention were described based on the embodiments in the drawings, but the present invention is not limited to this, and the constitution of each part can be replaced with an item of any constitution having the same functions. It is also possible to add any other constituent materials to the present invention.

Also, with the present invention, it is also possible to combine the constitutions (features) of any two or more of the embodiments noted above.

Also, with the aforementioned embodiments, an n type semiconductor layer was used as the first conductive region, and a p type semiconductor layer was used as the second conductive region, but with the present invention, this is not restricted to these, and it is also possible to use a p type semiconductor layer for the first conductive region and an n type semiconductor layer for the second conductive region.

Also, with the present invention, for the light source device, the light pulse generator can be a separate unit.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A photoconductive antenna adapted to generate terahertz waves when irradiated by pulsed light, the photoconductive antenna comprising:

a first conductive region made of a semiconductor material containing a first conductive type impurity;

a second conductive region made of a semiconductor material containing a second conductive type impurity different from the first conductive type impurity, the second conductive region being spaced apart from the first conductive region to form a gap therebetween in a top plan view of the photoconductive antenna; and a semiconductor region positioned in the gap between the first conductive region and the second conductive region in the top plan view, and made of a semiconductor material having a carrier density that is lower than a carrier density of the semiconductor material of the first conductive layer or a carrier density of the semiconductor material of the second conductive layer, an interfacial surface of the semiconductor region positioned in the gap being flush with a first interfacial surface of the first conductive region and a first interfacial surface of the second conductive region, and a second interfacial surface of the first conductive region positioned on an opposite side from the first interfacial surface and a second interfacial surface of the second conductive region positioned on an opposite side from the first interfacial surface being positioned on the same side with respect to the interfacial surface of the semiconductor region positioned in the gap.

2. The photoconductive antenna according to claim 1, wherein
the gap between the first conductive region and the second conductive region is filled by the semiconductor region.

3. A terahertz wave generating device comprising:
the photoconductive antenna according to claim 2; and
a light source configured and arranged to generate the pulsed light.

4. A camera comprising:
the photoconductive antenna according to claim 2;
a light source configured and arranged to generate the pulsed light; and
a terahertz wave detecting unit configured and arranged to detect the terahertz waves emitted from the photoconductive antenna and reflected by an object.

5. An imaging device comprising:
the photoconductive antenna according to claim 2;
a light source configured and arranged to generate the pulsed light;
a terahertz wave detecting unit configured and arranged to detect the terahertz waves emitted from the photoconductive antenna and transmitted through an object or reflected by the object; and
an image forming unit configured and arranged to generate an image of the object based on detection results of the terahertz wave detecting unit.

6. The imaging device according to claim 5, wherein
the image forming unit is configured and arranged to generate the image of the object using intensity of the terahertz waves detected by the terahertz wave detecting unit.

7. A measuring device, comprising:
the photoconductive antenna according to claim 2;
a light source configured and arranged to generate the pulsed light;
a terahertz wave detecting unit configured and arranged to detect the terahertz waves emitted from the photoconductive antenna and transmitted through an object or reflected by the object; and
a measuring unit configured and arranged to measure the object based on detection results of the terahertz wave detecting unit.

8. The measuring device according to claim 7, wherein
the measuring unit is configured and arranged to measure the object using intensity of the terahertz waves detected by the terahertz wave detecting unit.

9. The photoconductive antenna according to claim 1, further comprising
a first electrode disposed on the first conductive region and electrically connected to the first conductive region, the first electrode having the same shape as the first conductive region in the top plan view.

10. The photoconductive antenna according to claim 9, further comprising
a second electrode disposed on the second conductive region and electrically connected to the second conductive region, the second electrode having the same shape as the second conductive region in the top plan view.

11. The photoconductive antenna according to claim 1, further comprising
an insulation region disposed over at least a portion of the interfacial surface of the semiconductor region positioned in the gap between the first conductive region and the second conductive region in the top plan view.

12. A terahertz wave generating device comprising:
the photoconductive antenna according to claim 11; and
a light source configured and arranged to generate the pulsed light.

13. A camera comprising:
the photoconductive antenna according to claim 11;
a light source configured and arranged to generate the pulsed light; and
a terahertz wave detecting unit configured and arranged to detect the terahertz waves emitted from the photoconductive antenna and reflected by an object.

14. An imaging device comprising:
the photoconductive antenna according to claim 11;
a light source configured and arranged to generate the pulsed light;
a terahertz wave detecting unit configured and arranged to detect the terahertz waves emitted from the photoconductive antenna and transmitted through an object or reflected by the object; and
an image forming unit configured and arranged to generate an image of the object based on detection results of the terahertz wave detecting unit.

15. The imaging device according to claim 14, wherein
the image forming unit is configured and arranged to generate the image of the object using intensity of the terahertz waves detected by the terahertz wave detecting unit.

16. A measuring device comprising:
the photoconductive antenna according to claim 11;
a light source configured and arranged to generate the pulsed light;
a terahertz wave detecting unit configured and arranged to detect the terahertz waves emitted from the photoconductive antenna and transmitted through an object or reflected by the object; and
a measuring unit configured and arranged to measure the object based on detection results of the terahertz wave detecting unit.

17. The measuring device according to claim 16, wherein
the measuring unit is configured and arranged to measure the object using intensity of the terahertz waves detected by the terahertz wave detecting unit.

18. The photoconductive antenna according to claim 1, wherein
the semiconductor material of the semiconductor region is a III-V compound.

19. A terahertz wave generating device comprising:
the photoconductive antenna according to claim 1; and
a light source configured and arranged to generate the pulsed light.

20. A camera comprising:
the photoconductive antenna according to claim 1;
a light source configured and arranged to generate the pulsed light; and
a terahertz wave detecting unit configured and arranged to detect the terahertz waves emitted from the photoconductive antenna and reflected by an object.

21. An imaging device comprising:
the photoconductive antenna according to claim 1;
a light source configured and arranged to generate the pulsed light;
a terahertz wave detecting unit configured and arranged to detect the terahertz waves emitted from the photoconductive antenna and transmitted through an object or reflected by the object; and an image forming unit configured and arranged to generate an image of the object based on detection results of the terahertz wave detecting unit.

22. The imaging device according to claim 21, wherein the image forming unit is configured and arranged to generate the image of the object using intensity of the terahertz waves detected by the terahertz wave detecting unit.

23. A measuring device comprising:

the photoconductive antenna according to claim 1;

a light source configured and arranged to generate the pulsed light;

a terahertz wave detecting unit configured and arranged to detect the terahertz waves emitted from the photoconductive antenna and transmitted through an object or reflected by the object; and a measuring unit configured and arranged to measure the object based on detection results of the terahertz wave detecting unit.

24. The measuring device according to claim 23, wherein the measuring unit is configured and arranged to measure the object using intensity of the terahertz waves detected by the terahertz wave detecting unit.

\* \* \* \* \*